United States Patent [19]

Brundin et al.

[11] 4,019,059
[45] Apr. 19, 1977

[54] PATIENT'S SUPPORT ARRANGEMENT FOR AN X-RAY APPARATUS

[75] Inventors: Bengt Brundin, Sundbyberg; Wulf Trepte, Sollentuna, both of Sweden

[73] Assignee: Siemens Aktiengesellschaft, Erlangen, Germany

[22] Filed: Nov. 18, 1975

[21] Appl. No.: 633,161

[30] Foreign Application Priority Data

Nov. 22, 1974 Germany ............................ 2455447

[52] U.S. Cl. ............................... 250/451; 250/446; 250/449
[51] Int. Cl.[2] ............................................ G21K 508
[58] Field of Search ............... 250/444, 445, 445 T, 250/451, 456, 449, 490

[56] References Cited

UNITED STATES PATENTS

| | | | |
|---|---|---|---|
| 1,958,555 | 5/1934 | Wantz | 250/449 |
| 3,328,582 | 6/1967 | Morel | 250/446 |
| 3,396,274 | 8/1968 | Hogan | 250/456 |
| 3,473,024 | 10/1969 | Feiertag | 250/444 |
| 3,585,386 | 6/1971 | Horton | 250/451 |

*Primary Examiner*—Alfred E. Smith
*Assistant Examiner*—B. C. Anderson

[57] ABSTRACT

A patient's support arrangement for an X-ray apparatus, consisting of a patient's support pallet and a drive means for effecting the circular movement thereof about a horizontal rotational axis, as well as means for adjusting the support pallet in relationship to the rotational axis. Drive means for effecting the rotation of the support pallet or repository about a horizontal rotational axis located in the region of a patient resting thereon (isocentric movement) possesses a drive motor, as well as two servomotors with a control device for the control thereof and which consists of an arrangement for the setting of the reference values and a further arrangement for the determination of the actual values, as well as a servocontrol device for the correlation or balancing of reference and actual values whereby on a reference value transmitter, there are selectable the coordinates for the determination of the position of the patient rotational axis relative to the support pallet (patient coordinates), as well as the coordinates for the determination of the position of the virtual rotational axis within the movement space (spatial coordinates), and in which an actual value transmitter is associated with each servomotor for determination of the actual value of the patient support axis determined in patient coordinates in the spatial coordinate system, and which actuates the automatic control of the servomotors upon the incidence of a difference between the reference and actual value for the purposes of effecting a balancing therebetween.

6 Claims, 6 Drawing Figures

PATIENT'S SUPPORT ARRANGEMENT FOR AN X-RAY APPARATUS

FIELD OF THE INVENTION

The present invention relates to a patient's support arrangement for an X-ray apparatus, consisting of a patient's support pallet and a drive means for effecting the circular movement thereof about a horizontal rotational axis, as well as means for adjusting the support pallet in relationship to the rotational axis.

During neuoradiological examinations which require an injection of contrast media into the ventricle area carrying the cerebrospinal fluids, as for example, during encephalography, ventriculography and myelography, it is necessary that the patient can be moved about the area which is to be examined, so that the gravity-dependent contrast media flow becomes differentiable.

DISCUSSION OF THE PRIOR ART

A patient's support arrangement which is suited for this purpose is known form German Published Patent Specification No. 2,008,169, in which it is possible to effectuate an isocentric rotation of the support pallet about its horizontal support axis. However, it is disadvantageous that the rotational axis does not lie within the region of the patient, so as to lead to the result that the area; which is to be X-rayed is moved out of the X-ray path of the X-ray tube during each rotation, so as to thereby require a readjustment.

SUMMARY OF THE INVENTION

Accordingly, it is an object of the present invention to provide a patient's support arrangement in which it is possible to carry out a rotation about a suitable horizontal axis in the region of the patient without necessitating any readjustment.

The foregoing object is inventively achieved in that the drive means for effecting the rotation of the support pallet or repository about a horizontal rotational axis located in the region of a patient resting thereon (isocentric movement) possesses a drive motor, as well as two servomotors with a control device for the control thereof and which consists of an arrangement for the setting of the reference values and a further arrangement for the determination of the actual values, as well as a servocontrol device for the correlation or balancing of reference and actual values whereby on a reference value transmitter, there are selectable the coordinates for the determination of the position of the patient rotational axis relative to the support pallet (patient coordinates), as well as the coordinates for the determination of the position of the virtual rotational axis within the movement space (spatial coordinates), and in which an actual value transmitter is associated with each servomotor for determination of the actual value of the patient support axis determined in patient coordinates in the spatial coordinate system, and which actuates the automatic control of the servomotors upon the incidence of a difference between the reference and actual value for the purpose of effecting a balancing therebetween.

In a particular embodiment of the invention, the patient's support pallet is so constructed as to possess a pivot arm at whose free end there is fastened the support pallet so as to be pivotable about a rotational axis, there is supported within this axis a slide carriage which is movable along the longitudinal direction of the pivot arm, and wherein the drive motor actuates the pivot arm, whereas one of the servomotors actuates the pivotal movement of the support pallet and the other servomotor actuates the slide carriage. The advantage of this embodiment consists, above all, in that it is extremely light and may be constructed extremely compactly.

A further embodiment is particularly robust and can be constructed so as to be vibration-free even with patients of heavy body weights. In this embodiment, the patient's support arrangement consists of at least one vertical column which carries a vertically displaceable horizontal arm on which the support pallet is fastened so as to be pivotable about a horizontal axis which is displaceable along the longitudinal direction of the arm, whereby the drive motor actuates the pivotal movement of the support pallet and respectively one of the servomotors effects the movements of the axis of the support pallet and of the arm.

In a further feature of the invention, it is proposed that the patient support pallet consists of about three approximately equal parts, whose middle portion is fixedly connected with the horizontal axis, whereas the outer portions, of which one is constructed as a radiation-transmissive back support portion provided with a head support and the other a leg support portion provided with a pivotable foot support, are articulatedly connected to the middle portion, and that by means of swinging the back and leg support portions with respect to the middle portion of the patient support pallet, the latter is selectively usable as either a table as well as a chair. In that manner is achieved that, in the event of complications, the patient may be rapidly changed from a sitting into a reclining position, and that the cumbersome exchange of table and chair which, due to the heavy weights involved is possible only by means of special arrangements, can thus be readily avoided.

BRIEF DESCRIPTION OF THE DRAWINGS

Further advantages and details of the invention may now be ascertained from the following description of exemplary embodiments thereof, taken in conjunction with the accompanying drawings; in which.

DETAILED DESCRIPTION

Figure 1:
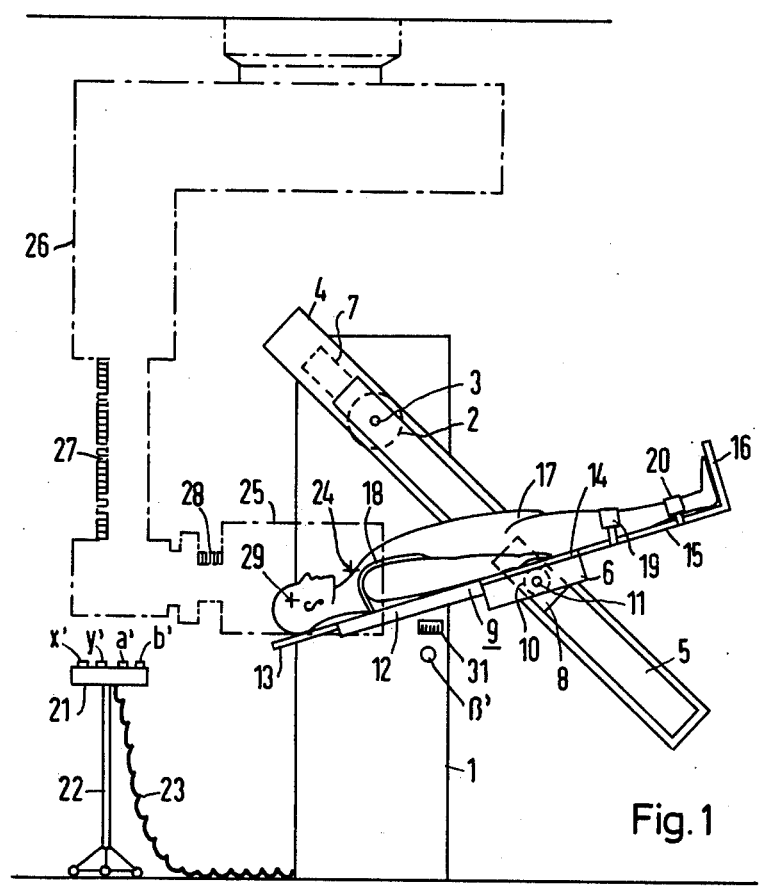
FIG. 1 illustrates a patient support arrangement whose actuating mechanism is operated pursuant to the principle of a polar coordinate system.

The patient's support arrangement as shown to FIG. 1 possesses a vertical support column 1 having a drive motor 2 arranged interiorly thereof, and on whose horizontally projecting drive shaft 3 there is pivotably fastened a U-shaped pivot arm 4. The interior of the U-profile 5 of the arm serves as the guide for a bracket 6. Additionally, a servomotor 7 is arranged therein which actuates the bracket 6, with the aid of a slide carriage 8, along the longitudinal direction of the pivot arm 4. In turn, the bracket 6 carries a patient's support pallet or repository 9 which is rotatable about the horizontal rotational axis 11 of the bracket 6, through the intermediary of a second servomotor 10. The patient's support pallet 9 is, additionally, manually adjustable in the direction of its rotational axis 11 through suitable means (not shown), and arrestable in its operative position.

The support pallet 9 consists of three elements which are articulatedly interconnected, namely, the back support portion 12 which is provided with an extensible radiation-permeable head support 13, the seat or middle portion 14, and the leg support portion 15 which possesses a pivotable foot support 16. For fastening of the patient 17 who is resting on the support pallet 9, provided thereon are the shoulder belt or strap 18, knee strap 19, and leg strap 20.

Figure 2:
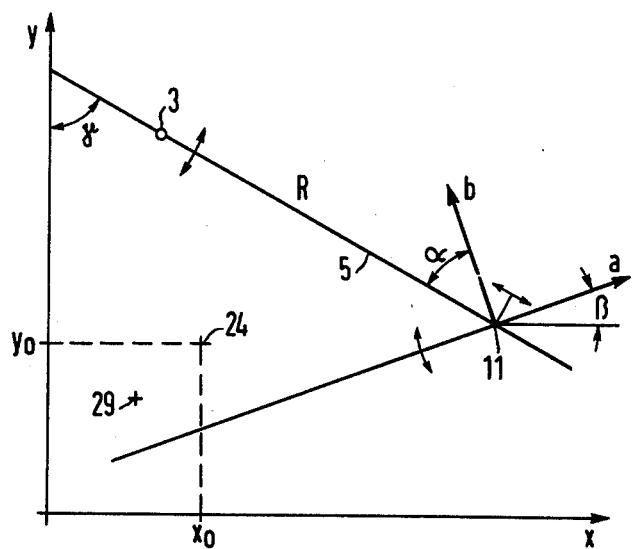
FIG. 2 is a corrdinate diagram whose plot of movements corresponds to that of the patient's support arrangement of FIG. 1.

FIG. 2 illustrates a coordinate graph or diagram whose principal construction conforms to the position of the patient's support arrangement in FIG. 1. Illustrated in this diagram are two rectangular coordinate systems $x/y$ as spatial coordinates and $a/b$ as patient coordinates; hereby the zero point of the system $a/b$ is located in the point or rotation 11 of the support pallet 9.

The coordinate system $a/b$ is movable along the line 5 which is identical with the imaginary median axis 5 of the pivot arm 4. The angle between the $x$-axis and the line a, which corresponds to the patient's support pallet 9, is designated with $\beta$, the distance between the axis of the drive shaft 3 and the rotational axis 11 of the line is designated with R, and the angle between the $y$-axis and the line 5 with $\gamma$. A further angle $\alpha$ between the line 5 and the $b$-axis of the coordinate system $a/b$ is equal to the difference between the angles $\gamma$ and $\beta$ ($\alpha = \gamma - \beta$). The point 24 is the reference value of the zero point of the spatial coordinate system $x/y$, and the marking 29 is the actual value of the zero point of the patient coordinate system $a/b$. The point 24 characterizes that point in space about which the patient within the patient's rotational axis 29 is to be moved isocentrically. The spatial point 24 can be marked by a light beam which is located on an X-ray tube-image generator combination 25. The coordinates thereof can be read off on the scales 27, 28.

Figure 3:
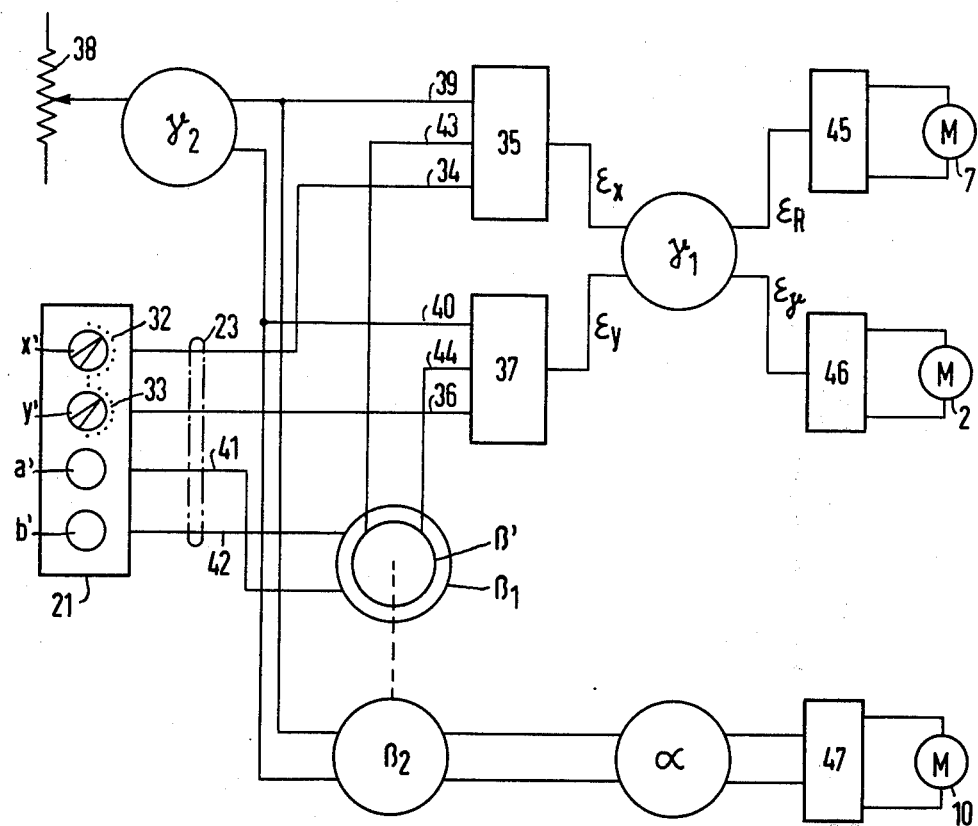
FIG. 3 is a circuit block diagram of the control system for a patient support arrangement operating in accordance with the principle of movement illustrated in FIG. 1.

The mentioned movements of the patient's support arrangement are controlled with the aid of an electrical control unit which is illustrated by the circuit block diagram of FIG. 3. A component of this control unit is a control box 21 which may be located either on a carriage 22, at any suitable location on the arrangement itself, or on a wall of the treatment chamber (FIG. 1). The control box 21, which is connected with the patient's support arrangement of a cable 23, possesses four rotary or turn knobs $x'$, $y'$, $a'$ and $b'$ for effecting the seting of the coordinates of two separate corrdinate systems, of which one ($x'$, $y'$) is associated with the X-ray tube-image generating combination 25, and the other one with the patient's support pallet 9. For the preparation of the initial adjustment of the patient, at first the physician will select the patient's rotary or turning axis 29, and then mark it on the patient 17.

Thereafter, with the aid of the light beam 24, that point ($x_o$; $y_o$) in the coordinate field $x$, $y$ (FIG. 2) is determined by means of which the point 29 is to be brought into rotation. The values of $x_o$ and $y_o$ can be read off on the scales 27, 28 on the X-ray support column 26 (FIG. 1). These values are then set with the aid of the turn knobs $x'$, $y'$ on the control box 21. The support pallet 9 is now controlled in such a manner through actuation of the turn knobs $a'$, $b'$ of the control box 21 through hereinbelow described means, that the marking 29 on the patient 17 coincides with the spatial point 24 which has been determined through the adjusted spatial coordinates $x_o$; $y_o$.

Through actuation of a rotary knob $\beta'$ which is arranged on the support arrangement, through the intermediary of similarly hereinbelow described means, there is carried out an isocentric movement of the patient 17 about the selected horizontal axis. An indicator arrangement 31 is associated with the rotary knob $\beta'$, which indicates the present angle of the patient support pallet 9 with respect to the horizontal position thereof. Utilized as actual value transmitters are function generators which are arranged on the rotational axes 3 and 11 (FIG. 1) and whose output signals correspond to the sine and cosine of the rotational angle of the associated rotational axes. Furthermore, a potentiometer 38 is so located within the pivot arm 4 whereby the resistance value thereof is proportional to the distance between the rotational axes 3 and 11. The remaining components of the control system are described hereinbelow.

The turn knobs $x'$ and $y'$ of the control unit 12 are initially set to those values on the currently associated scales 32, 33 which are to be read off on the scales 27, 28 for, respectively, the horizontal and the vertical positions of the isocentrum 24. The electrical signal $x_o$ corresponding to the horizontal position of the isocentrum 24 is transmitted through the conduit 34 to the cable 23 of the control circuit 35. The $y_o$-signal which corresponds to the vertical position of the isocentrum 24 is transmitted through the conduit 36 to the control circuit 37. The output signal of the potentiometer 38 is dependent upon the distance R between the rotational axes 3 and 11.

In the function generator $\gamma$ 2 which is located on the rotational axis 3, the value for the distance R is multiplied with the sine, or respectively, cosine of that angle which at that time has been assumed by the pivot arm 4. The produce R sine $\gamma$ reaches the control circuit 35 through the connecting conduit 39, and the product R cosine $\gamma$ reaches the control circuit 37 through the connecting conduit 40. These signals are then transmitted to the present control circuits 35, 37.

Through actuation of the turn knobs $a'$ for the horizontal and $b'$ for the vertical movement of the support pallet, which are arranged on the control box 21, the marking 29 on the patient 17 is conveyed to the isocentrum 24 through intermediary of the motors 2, 7 and 10. The values of the turn knobs $a'$, $b'$, in a similar manner, are converted into electrical signals and transmitted to the function generator $\beta 1$ through the conduits 41, 42.

The electrical values $a$, $b$ which are applied to the function generator $\beta 1$ are then multiplied with the output values thereof. Thus, there is transmitted to the control circuit 35 through the connection 43 the signal a cosine $\beta - b$ sine $\beta$, and the control circuit 37 through the connection 44 the signal $b$ cosine $\beta + a$ sine $\beta$.

The reference values $x_o$, $y_o$ which are transmitted to the control circuits 35 and 37 are now compared with the introduced actual values. As a result, the following equation is produced in the control circuit 35:

$$\Sigma_x = x_o - (R \sin \gamma + a \cos \beta - b \sin \beta)$$

and in the control circuit 37 the following equation:
$$\Sigma_y = y_o - (R \cos \gamma + b \cos \beta - a \sin \beta)$$

The differential signals $\Sigma x$ and $\Sigma y$, which are produced when the actual and refernce values are different, are utilized in order to control the servomotors 7 for the longitudinal displacement of the bracket 6, and the servomotor 2 for effecting the rotation of the pivot arm 4. Since the control of these motors must be carried out in conformance with the magnitude of the angle, at first the $\Sigma x$ and $\Sigma y$ signals must be however, transmitted to a further function generator $\gamma 1$ which is fastened to the rotational axis 3. The output signals of these function generators are then determined as follows:

$$\Sigma_R = \Sigma x \sin \gamma - \Sigma_y \cos \gamma$$

$$\Sigma \gamma = x \cos \gamma + \Sigma_y \sin \gamma$$

These signals are then transmitted to the currently associated signal amplifiers 45, 46, and subsequently to the motors 2, 7. These motors are actuated for so long until a correlation or balancing has taken place between the actual and reference values.

The angle $\alpha$ is controlled through the servomotor 10 in correspondence with the difference between the output signals of the function generator $\gamma 2$ and $\beta 2$ ($\alpha = \gamma 2 - \beta 2$). This signal is then transmitted to the motor amplifier 47, whereby the servomotor 10 is driven for so long until $\alpha = 0$. The function generator $\alpha$ is arranged on the rotational axis 11 and the function generator $\beta 2$ on the $\beta 1$-axis.

When the function generator $\beta 1$ is adjusted by means of the turn knob $\alpha'$, then the output signal thereof varies in such a manner whereby the motors 7, 2 and 10, as previously described, control the movement of the pivot arm 4, the bracket 6 and the patient's support pallet 9 in such a functional interdependence, so that there results an isocentric movement about the axis 24. The isocentric movement is speed-controlled, meaning dependent upon the speed of rotation of the function generator $\beta 1$, in which the rotational angle is additionally selectable.

The patient support pallet is transportable at a suitable constant angle along its longitudinal direction (transversal movement) and perpendicular thereto. This is carried out through actuation of the turn knobs $a'$ and, respectively, $b'$.

Figure 4:
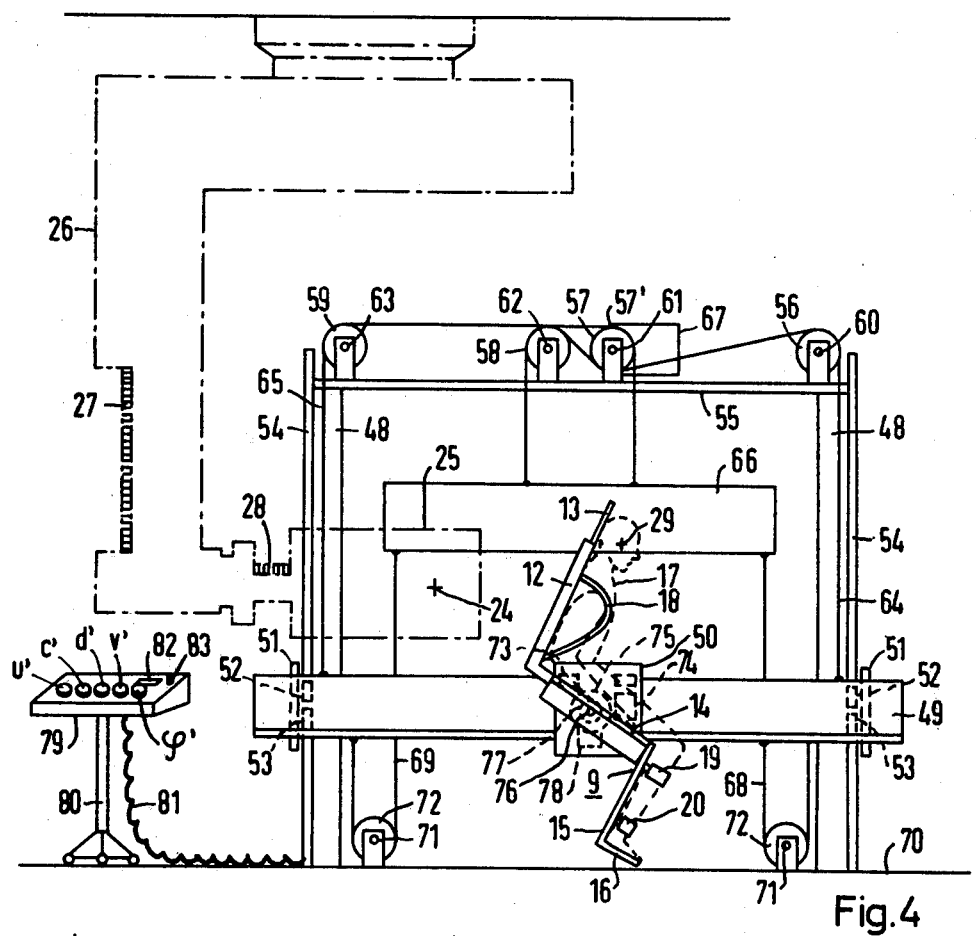
FIG. 4 is a patient's support arrangement whose actuating mechanism is operated pursuant to the principle of a rectangular coordinate system.

FIG. 4 shows a further embodiment of a patient's support arrangement, whose actuating mechanism is operated in accordance with the principle of a rectangular coordinate system. The arrangement consists of two vertical columns 48, which support a vertically displaceable horizontal beam 49. The beam 49 in turn supports the support pallet 9 which is transportable through intermediary of the movable frame 50 along the longitudinal direction of the arm.

Fastened in the region of the two ends of the beam 49 are carriages 51 with their presently associated rollers 52, 53, which are vertically guided along rails 54 fixedly supported on the columns 48. The upper ends of the columns are connected by means of a crossbeam 55 on which there are arranged five sprocket wheels 57' and 56 through 59 and rotatably supported on the axes 60 through 63. The beam 49 is connected with a counterweight 66 through the chain hoists 64, 65 for weight unloading. The chain hoist 64 is fastened to the upper surfaces of the beam 49, runs above the sprocket wheel 56, below the wheel 57, then again above the sprocket wheel 58, and is then fixedly arranged on the upper side of the counterweight 66. The chain hoist 65, which is similarly located on the upper surface of the beam 49, runs above the sprocket wheel 59 and above the sprocket wheel 57' which is located on the axis 61 behind the wheel 57, and is finally fastened to the upper surface of the counterweight 66. The beam is additionally connected with the counterweight through the chain hoists 68, 69, which run below sprocket wheel 72 arranged on the floor 70 and which are rotatable through the linkage points 71.

The transport frame 50 with the support pallet 9 possesses rollers 73 which run on both sides of the beam 49, and through which there is driven a servomotor 74 located in the frame. For effecting the pivoting movement of the support pallet 9 there is provided a drive motor 75. The patient's support pallet 9 additionally is displaceable along the direction of its rotational axis 76 by means of a spindle 77 which is displaceable through the motor 78 which, similarly to the drive motor 75 is arranged within the frame 50, and is arrestable in the presently desired operative position.

As may be ascertained in FIG. 4, the elements 12, 14, 15 with the foot support 16 of the patient's support pallet 9 are so adjustable that the support plate is usable as a patient's chair. The angle of inclination of the back supporting portion 12 and the foot supporting portion 15 with the foot support 16 as compared to the middle portion 14 is adjustable through the use of known means, thereby not shown.

The movements of the patient's support arrangement, as in the embodiment illustrated in FIG. 1, are controlled with the aid of a hereinbelow further described electrical control unit. Also in this instance, a component of the control unit is a control box 79 which, for example is located on a frame 80. The control box 79 is connected with the patient's support arrangement by means of a cable 81. The box 79 possesses four turn knobs $u'$, $v'$, $c'$, $d'$ for the setting of the coordinates of two separate coordinate system, of which one ($u'$, $v'$) is associated with the plane of movement of the support pallet (spatial coordinates) and the other with the support plane of the patient on the support pallet 9 (patient coordinates). The initial positioning of the patient, as described with respect to FIG. 1, may be set by means of the rotational point 29 marked on the patient 17 by the physician, and the desired spatial point 24 as the initial position for commencing the isocentric movement of the patient. The spatial coordinates are selected by means of the turn knobs $u'$, $v'$ on the control box 79. The support pallet is now so controlled through actuation of the turn knobs $c'$, $d'$ of the control box 79 through hereinbelow described means, whereby the point 24 coincides with the marking 29 on the patient 17.

Through actuation of a further turn knob $\phi'$ which is located on the control box 79 there is then effected, through similarly hereinbelow described means, an isocentric movement of the patient through the point 29 about the selected virtual horizontal rotational axis.

Precisely as in the embodiment shown in FIG. 1, the rotary knob $\phi'$ has an indicator arrangement 82 associated therewith, which indicates the present angle of the patient's support pallet 9 in comparison with the horizontal position thereof. The support pallet 9 additionally is adjustable in the direction of its rotational axis 76, through pressing of the knob 83 on the control box 79.

Figure 5:
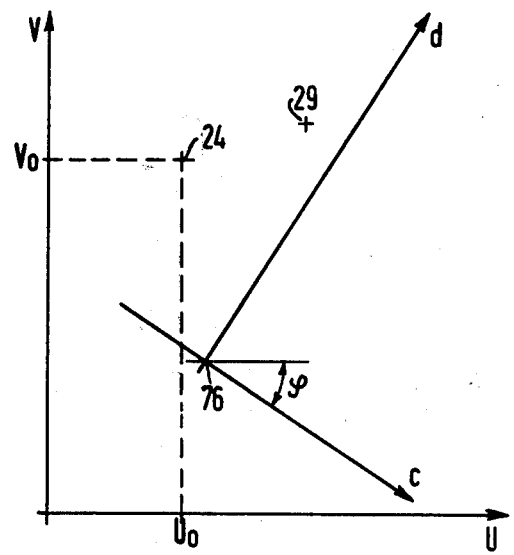
FIG. 5 is a coordinate diagram whose plot of movements corresponds to that of the patient's support arrangement of FIG. 4.
Figure 6:
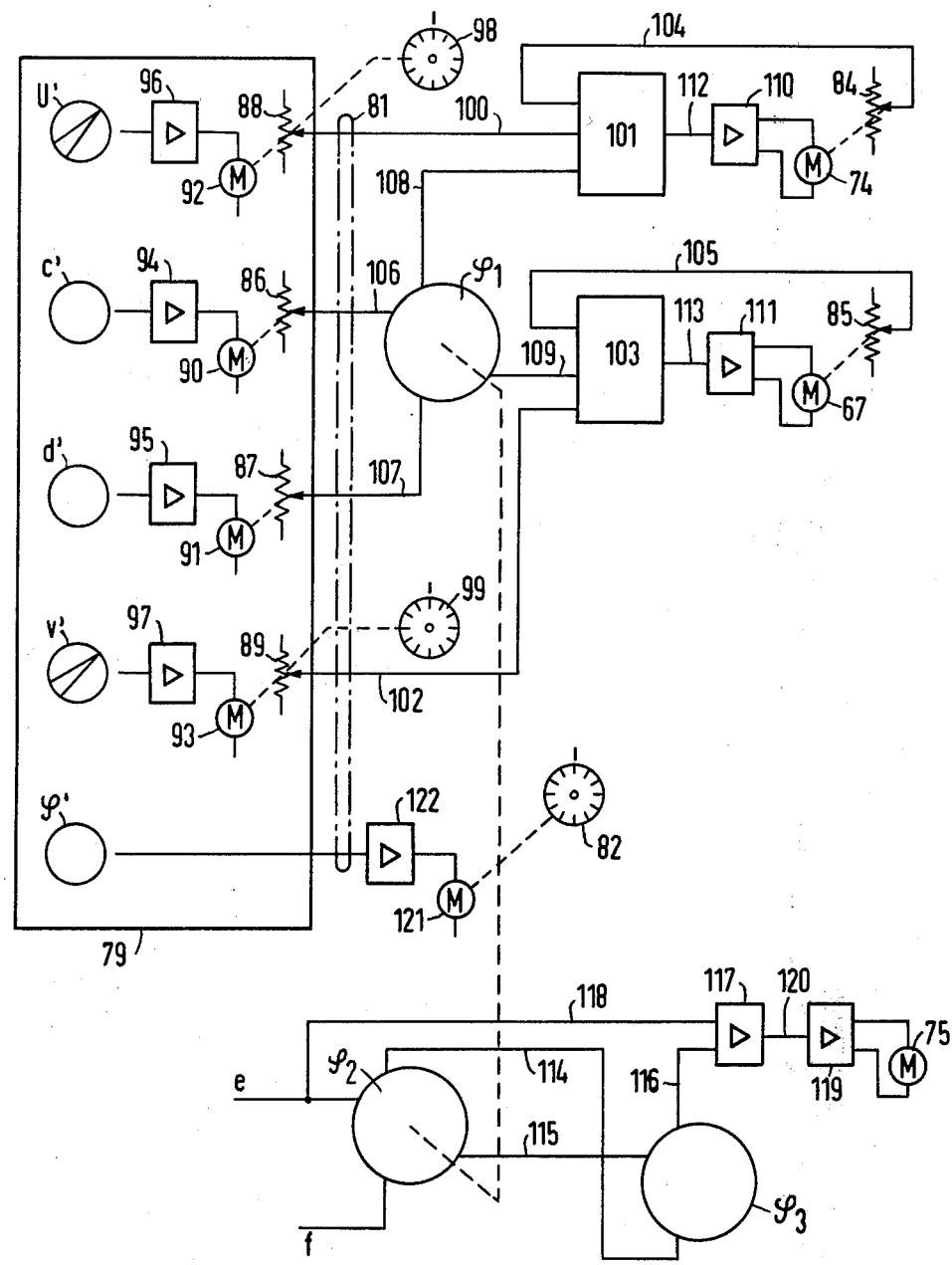
FIG. 6 is a circuit block diagram of a control system for a patient's support arrangement operating in accordance with the principle of movement illustrated in FIG. 4.

FIG. 5 illustrates a coordinate graph or diagram whose principle construction corresponds to the patient's support arrangement of FIG. 4. The coordinate diagram consists of the coordinate system with the spatial coordinates u/v and the patient corrdinates c/d; hereby the zero point of the system c/d is located within the rotational point 76 of the support pallet 9. The angle between the axes u and c is designated by $\phi$, and the horizontal rotational axis about which the body of the patient 17 is to rotate, is again designated by 29, and the spatial point with 24. The digram is explained in greater detail in connection with the circuit block diagram of the control circuit of FIG. 6 with respect to the support arrangement shown in FIG. 4.

Pursuant to this block diagram, as the actual value transmitter are employed the potentiometers 84, 85, which are arranged on the servomotors 67 and 74 for effecting the respectively vertical and horizontal movements of the support arrangement 9. The potentiometers 84, 85 are so located that the resistance values thereof are proportional to the position of the beam 49 or, respectively, the transport frame 50 for the support pallet 9. The remaining components of the control system are described later on hereinbelow.

The parameters $c'$, $d'$, $u'$, $v'$ are set by means of the motor-driven potentiometers 86 through 89. Through these speed-controlled motors 90 through 93, which are presently connected to a signal amplifier 94 through 97, it is possible to attain a rapid, smooth and precise positioning of the support pallet.

The turn knobs $u'$ and $v'$ on the control box 79 are set on the scales 98, 99 to such values which are then read off on the scales 27, 28 (FIG. 4) for, respectively, the horizontal and the vertical positions of the isocentrum. The electrical signal $u_o$, corresponding to the horizontal position of the isocentrum, is transmitted through the conduit 100 to the cable 81 of the control circuit 101. The $v_o$-signal, which corresponds to the vertical position of the isocentrum, is transmitted through the conduit 102 to the control circuit 103. The output signals of the potentiometers 84, 85 are dependent upon the position of the beam 49, respectively, the transport frame 50. The values which corresponds to these positions (actual values) reach the control circuits 101, 103 through the connecting conduits 104 (u-actual) and 105 (v-actual). These signals are then transmitted to the present control circuits 101 and 103.

Through actuation of the turn knobs $c'$ and $d'$ located on the control box 79 for effecting the movement of the control pallet along its longitudinal direction (transversal movement) and perpendicular thereto, the marking 29 on the patient 17 (FIG. 4) is conducted by means of the motors 67 and 74 to the isocentrum 24. The values of the turn knobs $c'$, $d'$ are converted into electrical signals in a corresponding manner, and then transmitted to the function generator $\phi$1 through the conduits 106, 107.

The electrical values c, d which are transmitted to the function generator $\phi$1 are then multiplied with the output values thereof. Thus, there is transmitted to the control circuit 101 through the connection 108 the signal $c \cos \phi + d \sin \phi$, and to the control circuit 103 through the connection 109 the signal $d \cos \phi - c \sin \phi$. First, calculated in the control circuits 101, 103 the differential signals of the reference values. As a result thereof, the following equation becomes effective in the control circuit 101:

$$u \text{ ref.} = u_o - (c \cos \phi + d \sin \phi)$$

and the following equation in the control circuit 103:

$$v \text{ ref.} = v_o - (d \cos \phi - c \sin \phi)$$

The differential signals $\Sigma u$ and $\Sigma v$ meaning the output signals of the control circuits 101, 103, which are then produced when the actual values and reference values are different, are employed in order to control the servomotor 74 for effecting the horizontal movement of the support pallet 9 and the servomotor 67 for the vertical movement of the beam 49. The output signals of these control circuits are then obtained as follows:

$$\Sigma_u = u \text{ ref.} - u_{act}$$

$$\Sigma_v = v \text{ ref.} - v_{act}$$

The signals are then transmitted to the presently associated signal amplifiers 110, 111 through the conduits 112, 113, and subsequently to the motors 74, 67, The motors are actuated for so long until a balancing has taken place between the actual and reference values.

The rotor of the function generator $\phi$1 is connected with the rotor of a second function generator $\phi$2. Both are so coordinated with each other whereby their output signals have the same phase position. The function generator $\phi$2 has constant voltage signals e and f transmitted thereto in relation to the function generator $\phi$1. The output signals (reference values) of the function generator $\phi$2 are transmitted through the conduits 114, 115 to a further function generator $\phi$3 which is located on the rotational axis 76 of the support pallet 9. In this function generator there takes place a difference formation between the signals (reference values) transmitted thereto through the conduits 114, 115, and the angle value (actual value) produced by the rotor of the function generator $\phi$3. The output signal of the function generator $\phi$3 is transmitted through the conduit 116 to a control circuit 117, which also has transmitted thereto through the conduit 118 the constant signal e. The output signal of this control circuit is determined in accordance with the formula $$\Sigma \phi = \phi \text{ ref} - \phi \text{ act.}$$

The signal is then transmitted through the conduit 120 to the signal amplifier 119, and subsequently to the motor 75, wherein the motor is driven for so long until $\Sigma \phi = 0$.

When the function generators $\phi$1 and $\phi$2 are adjusted by means of the turn knob $\phi'$ through the speed-controlled motor 121 with the associated signal amplifier 122, the output signals thereof are so varied whereby the motors 67, 74 and 75, as previously described, control the movement of the beam 49, the transport frame 50, and the patient's support pallet 9 in such a functional interdependence, that an isocentric movement is carried out about the axis 24. The isocentric movement also in this example is speed-controlled, meaning dependent upon the speed or rotation of the function generators $\phi 1$ and $\phi 2$. The rotational angle $\phi$ is additionally selectable.

When the position of the X-ray tube-image generator combination 25 is changed manually, (new isocentrum), the new position of the apparatus 26 is read off on the scales 27, 28 and correspondingly set by means of the turn knobs $u'$, $v'$. Through rotation of these knobs there is produced a difference between the actual and reference values which is transmitted to the motors 67 and 74, whereby these are actuated for so long until the marking on the patient has reached the new isocentrum, without acutating the turn knobs $c'$ and $d'$.

While there has been shown what is considered to be the preferred emboidment of the invention, it will be obvious that modifications may be made which come within the scope of the disclosure of the specification.

What is claimed is:

1. In a patient's support arrangement for an x-ray apparatus, including a support pallet for supporting a patient thereon; drive means for effecting circular movement of said pallet about a horizontal rotational axis; and means for adjusting said pallet relative to said rotational axis, the improvement comprising: said drive means comprising two servomotors for rotating said pallet about said horizontal axis in the region of a patient resting thereon; control means for controlling said servomotors, said control means including means for setting of reference values of the coordinates in space of the desired position of said rotational axis, sensing means in said control means for sensing of actual values of the coordinates of the acutal position of said rotational axis, follow-up contro means for actuating said servomotors when a difference prevails between said desired position and said actual position, said servo motors being acutated in directions for reducing said difference; said means for setting said reference values transmitting the desired position of said rotational axis in terms of coordinates of said support pallet, the coordinates of said support pallet corresponding to the coordinates of the patient, said reference values being in a coordinate system separate from the coordinate system of the position of said patient.

2. An X-ray apparatus as claimed in claim 1, said support arrangement comprising a pivot arm having a free end, said pallet being supported on said free end so as to be pivotable about a horizontal axis; a slide carriage supporting said axis being movable in the longitudinal direction of said pivot arm, said drive motor actuating said pivot arm, one of said servomotors effectuating the pivoting movement of said pallet, and the other servomotor actuating said slide carriage.

3. An X-ray apparatus as claimed in claim 1, said support arrangement comprising at least one vertical column; a vertically displaceable horizontal beam being supported on said column, said pallet being pivotably fastened to said beam and displaceable along the longitudinal direction thereof, said drive motor effectuating the pivoting movement of said pallet, and one of said servomotors each respectively effecting the movements of the axis of the pallet and of said beam.

4. An X-ray apparatus as claimed in claim 3, comprising motor-driven means for displacing said pallet in the direction of its rotational axis and arresting the pallet in its present operative position.

5. An X-ray apparatus as claimed in claim 2, said patient's support pallet comprising three approximately equal parts including a middle and two exterior parts, said middle part being fixed connected to said horizontal axis, one said exterior part being a back-supporting portion having a radiation-permeable head support, the other exterior part being a leg-supporting portion having a pivotable foot support, said exterior parts being articulateldy connected to said middle part whereby said pallet can be selectively utilized as a table or a chair through pivoting of said back-supporting portion and said leg-supporting portion relative to said middle part.

6. An X-ray apparatus as claimed in claim 1, said actual value and reference value transmitter respectively comprising function generators.

* * * * *